United States Patent [19]

Kawai et al.

[11] 4,433,299

[45] Feb. 21, 1984

[54] METHOD AND APPARATUS FOR MEASURING INTERFACIAL ELECTROKINETIC PHENOMENA

[75] Inventors: Yoshio Kawai, Musashino; Kiyoshi Kitagawa, Komae, both of Japan

[73] Assignee: Kureha Kagaku Kogyo Kabushiki Kaisha, Nihonbashi, Japan

[21] Appl. No.: 238,822

[22] Filed: Feb. 27, 1981

[30] Foreign Application Priority Data

Mar. 7, 1980 [JP] Japan ................................. 55-28915
Jan. 26, 1981 [JP] Japan ................................. 56-9799

[51] Int. Cl.³ ........................................... G01N 27/62
[52] U.S. Cl. ................................. 324/464; 324/71.1; 204/180 R; 204/299 R
[58] Field of Search .................... 324/464, 71 R, 442, 324/445, 449; 204/180 R, 299 R; 422/68; 73/863, 863.21

[56] References Cited

U.S. PATENT DOCUMENTS

| | | | |
|---|---|---|---|
| 2,495,297 | 1/1950 | Stern | 324/71.5 |
| 3,806,893 | 4/1974 | Ohnishi et al. | 324/71 R |
| 3,993,945 | 11/1976 | Warmoth et al. | 324/449 |

Primary Examiner—Michael J. Tokar
Assistant Examiner—Kevin D. O'Shea
Attorney, Agent, or Firm—Wegner & Bretschneider

[57] ABSTRACT

A method and apparatus are disclosed for measuring interfacial electrokinetic phenomena such as electrophoresis by applying stationary electric field to a sample, wherein the voltage between two points in the sample other than the electrodes for an electric current application is detected and the electric current is supplied to the sample to maintain the detected voltage constant, and the sample is preheated while the particles being substantially kept in a stationary state by applying an alternating voltage prior to the application of the stationary voltage, to thereby obtain the mobility of the charged particle in the sample at high accuracy.

9 Claims, 12 Drawing Figures

METHOD AND APPARATUS FOR MEASURING INTERFACIAL ELECTROKINETIC PHENOMENA

DETAILED DESCRIPTION OF THE INVENTION

This invention relates to a method and apparatus for measuring interfacial electrokinetic phenomena such as electrophoresis and electroosmosis. More specifically, this invention relates to the measurement of the electroosmotic phenomena, that is, the measurement of the fluidity of liquid resulted from the movement of the solvent accompanying the migration of ions in the diffusion double layer in the case where an electric field is applied along a solid-liquid interface or a liquid-liquid interface, or for the measurement of the moving speed of electric charged particles in an electric field.

As the apparatus for measuring the interfacial electrokinetic phenomena, an electrophoretic apparatus observing the movement of charged particles has been well known in the field of art concerning micro particles having surface charge.

In the electrophoretic apparatus mentioned above, a stationary electric field is produced in a migration chamber (electrophoresis cell) by applying a constant voltage between a pair of electrodes disposed in the migration chamber and the charged particles in the chamber are moved in accordance with the electric field. For example, the moving speed of the particles are observed and measured by means of a microscope coupled with an optical source. The electrophoretic mobility obtained through measurement by the electrophoretic apparatus is represented by the speed of each of the particles per intensity of the electric field (micron/sec per v/cm). It is, accordingly, significant for the measurement of the electrophoretic phenomena to supply an essentially constant electric field to a sample to be measured and to hold a sample at the constant temperature in order to obtain highly accurate measured values, and this is an important problem.

Since a potential difference often exists between the two electrodes even if no electric field is applied externally, the current flowing in the sample is frequently different depending on the directions of the electric field.

Consequently, in a case where a constant voltage power source is employed, for example, as the power source for the application of the electric field, although the voltage between a pair of electrodes in the electrophoretic apparatus can be kept constant, the potential gradient (gradient in the electric field intensity) in the migration chamber, for example, the resulting voltage drop between the sample to be measured and electrode is not always constant. Thus, since the voltage applied to the sample itself is not actually constant, accurate measuring values can not be obtained.

Accordingly, it is generally preferred for the use of a constant current power source rather than the use of a constant voltage power source for the measurement of electrophoretic mobility, in which the intensity of the electric field is determined by the calculation of the product of the current and the electrical resistance of the sample per unit distance. The measurement under the condition of constant temperature is also indispensable in this case.

In order to make the temperature constant in the migration chamber, means for recycling heat from the medium to the outside of a measuring cell that forms a migration chamber and keeping the temperature of the medium constant is generally employed. However, such a measure still involves those disadvantages including that no rapid response is possible for the generation of Joule heating in the sample to be measured caused by the DC (direct current) for the application of the electric field. Thus, the foregoing problems can not yet be solved.

The fundamental operation procedures to measure the electrophoretic mobility are as follows:

1. A sample to be measured is introduced into a measuring cell.
2. When the fluctuation of particles in the sample in the measuring cell is settled, the sample is microscopically observed to determine a particle to be measured.
3. DC is supplied to start the flow of the particle.
4. When the flow of the particle is settled to a stationary state after the application of the DC, the mobility of the particle, that is, the moving distance per unit time is measured.
5. After the completion of the measurement, the polarity of the DC is reversed and the same procedures as those in the paragraphs 3 and 4 above are conducted to measure the mobility of the particle in the opposite direction.
6. The average value for the mobility as measured in the paragraphs 4 and 5 is determined as the electrophoretic mobility for the particle.

The procedures described in the paragraphs 2 to 6 are repeated again for several tens to several hundreds of particles and the average value obtained therefrom is determined as the average mobility for the particles in the sample.

The time in which the particle flow is stabilized in the procedure described in the paragraph 4 is about 0.1–0.2 sec. However, the temperature of the sample in the measuring cell is raised by the Joule heating generated by the supply of the measuring DC and generally it takes from ten and some up to several hundreds sec depending on the cell structure to stabilize the temperature of the sample. Accordingly, although the actual measuring time for the mobility is within 1–3 sec. per one step, the time necessary for one measurement step is from ten and sometimes up to several hundreds sec if the measurement is to be started after the settling of the temperature, which is very time consuming. Further, the particles to be measured continue to move in one direction while waiting for the stabilization of the temperature under the supply of the measuring DC, and most of the particles get out of view or the particles move in one direction in the electrophoretic measuring method using a microscope. Thus, it has been impossible to conduct measurement at high accuracy under constant temperature.

An object of this invention is to obtain measured values at high accuracy under the condition of constant temperature.

Another object of this invention is to perform measurement at high accuracy in a short time.

A further object of this invention is to perform measurement at high accuracy by compensating the changes in the electrical resistance accompanying the changes in the temperature of the sample to be measured thereby continuing to apply an essentially constant voltage to the sample.

In order to obtain the foregoing object, this invention provides a method of measuring interfacial electrokinetic phenomena by the application of stationary electric field to a sample to be measured, wherein the method comprises a step of controlling measuring conditions inside the migration chamber, as well as a measuring apparatus wherein a power source system for the application of the electric field to a sample in the chamber to be measured comprises a function of controlling measuring conditions.

This invention provides a method of measuring the interfacial electrokinetic phenomena in which AC (alternating current) power is supplied to a sample to be measured prior to the supply of the stationary electric field to the sample so that electric power is dissipated in said sample by an amount substantially equal to that of the electric power to be dissipated therein upon application of the stationary electric field, as well as the apparatus for measuring the interfacial electrokinetic phenomena wherein the power source system for applying the electric field to a sample to be measured comprises an output selection circuit for selecting either a DC power source or an AC power source.

Specifically, this invention enables the temperature of a sample to be measured always at the a constant level upon measurement of the mobility of the particles, by continuously supplying an AC to the sample while DC for the measurement of the electrophoresis is not being supplied to the sample, that is, in the interval between the successive measurement steps so that electric power is dissipated in the sample by an amount equal to that of the electric power to be dissipated by the measuring DC in the cell.

For the AC power used in the measurement of electrophoresis according to this invention, it is desired that the AC is of such a frequency that the movement of the particles can be regarded as being in a stationary state in view of the easy determination of the particles to be measured, and usually the frequency is suitably more than 10 Hz.

This invention provides a method of measuring the interfacial electrokinetic phenomena by the application of electric field to a sample to be measured in which voltage between two points in the positions other than the electrode for the voltage application in the sample and applying the voltage to the sample under the current control so as to always make the detected voltage constant, as well as an apparatus for measuring the electrophoresis which comprises a pair of spaced voltage detection probes disposed in the migration chamber of the electrophoretic apparatus, the voltage between the voltage detection probes being fed back to the power source system through its terminals connected to the detection probes and further comprises a DC power source for controlling the current flowing to the current output terminals connected to a pair of opposed electrodes of the electrophoretic apparatus so as to maintain the voltage between the probes to a constant level. The intensity of the electric field can thus be made constant following after the changes in the electrical resistance of the sample to be measured to thereby render the electric field intensity constant and improve the measuring accuracy significantly.

This invention can be applied not only to the measurement of the electrophoresis using a microscope but also to the measurement of electrophoretic phenomena or the measurement of electroosmosis using detector-doppler method. The method and apparatus for measuring the interfacial electrokinetic phenomena according to this invention can obtain measured values at high accuracy by the application of an essentially constant voltage to a sample to be measured with no effects from the Joule heating generated by supplied current and the like.

This invention is to be explained by way of its preferred embodiments referring to the accompanying drawings, by which the foregoing objects and features, as well as other objects and features of this invention will be made more clear, wherein FIG. 1 is a schematic view of an electrophoretic measuring apparatus as a first embodiment according to this invention;

Figure 1:
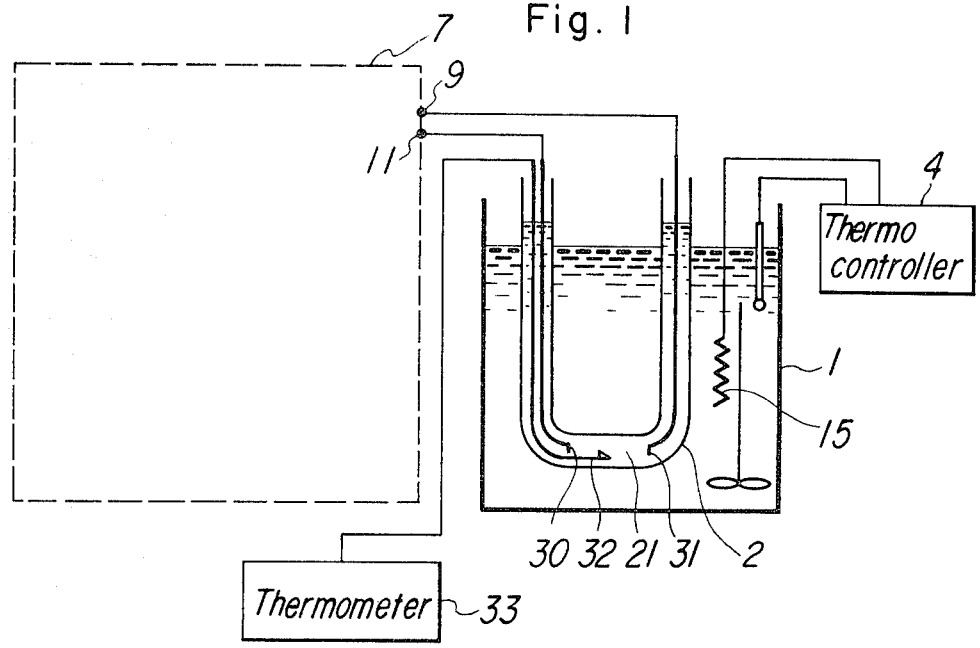

As shown in FIG. 1, the electrophoretic measuring apparatus which is a first embodiment of this invention is placed in a temperature constant bath 1, and comprises a U-shaped glass tube 2 constituting a migration chamber, a pair of electrodes 30, 31 disposed with 50 mm gap to each other at the bottom of the U-shaped glass tube 2 and a power source 7 for supplying electrical current to the electrodes 30, 31.

The U-shaped glass tube 2 is of 2 mm inner diameter and filled with a sample 21 to be measured. A sheathed thermocouple 32 of 0.25 mm outer diameter covered with a polyethylene tube is disposed about in the middle of the inside of the glass tube and connected to a temperature indicator (thermometer) 33 for monitoring the temperature in the U-shaped glass tube 2.

Figure 2:
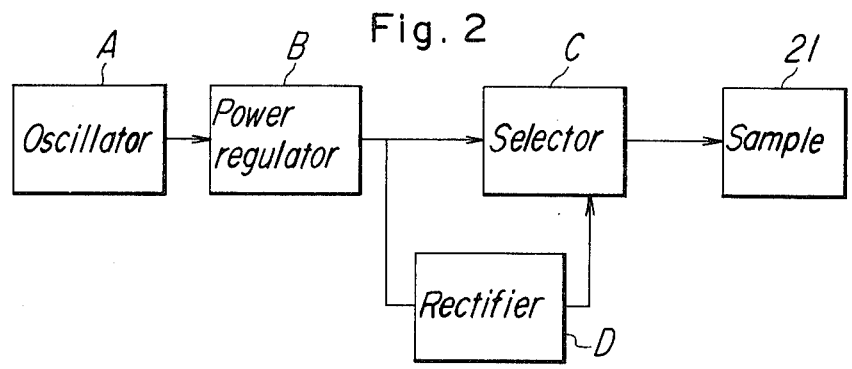
FIG. 2 and FIG. 3 are block diagrams for another power source systems for use with this invention.

As shown in FIG. 2, the power source system 7 comprises a rectangular waveform generator (oscillator) A, a power controller or regulator B, an output selection circuit C and a rectifier circuit D. The power source system is constituted such that the rectangular waveform produced from the rectangular waveform generator A is regulated by the power regulator B, passed through the rectifier circuit D depending on the indication from the output selection circuit C which determines either to convert the output into DC or supply it as it is as AC and then supplied by way of the electrodes 30, 31 for applying an electric field to the sample 21.

After setting the sample 21 in such a measuring apparatus, the power source 7 is put to ON to apply the electric field. The output selection circuit C of the power source system 7 is designed such that the AC is at first supplied to the sample 21 for a predetermined of time and then the DC is supplied to the sample 21. The mobility of the particles in the sample is measured during supply of the DC.

Figure 3:
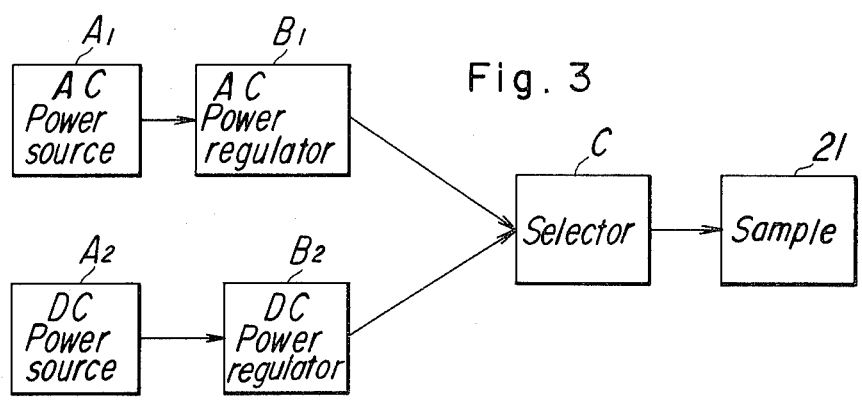

As shown in FIG. 3, the power source may be composed of an AC power source $A_1$ and a DC power source $A_2$, instead of the generator A in FIG. 2, and each of the power sources may be connected by way of output regulation circuits (power regulator) $B_1$, $B_2$ to an output selection circuit C.

Since the mobility can be measured at a constant temperature by the use of the measuring method and apparatus according to this invention, generation of errors resulted from the temperature change is prevented and the measuring accuracy can be improved significantly.

Further, since repeated measurements usually required can be performed by repeating the procedures of determining particles to be measured under the AC application state, switching the AC directly to the DC and measuring the mobility of the particles, time for the stabilization of temperature is no longer necessary as in conventional apparatus and the measuring time can be shortened remarkably. The rectangular waveform generator can be substituted with commercial AC power source.

Figure 4:
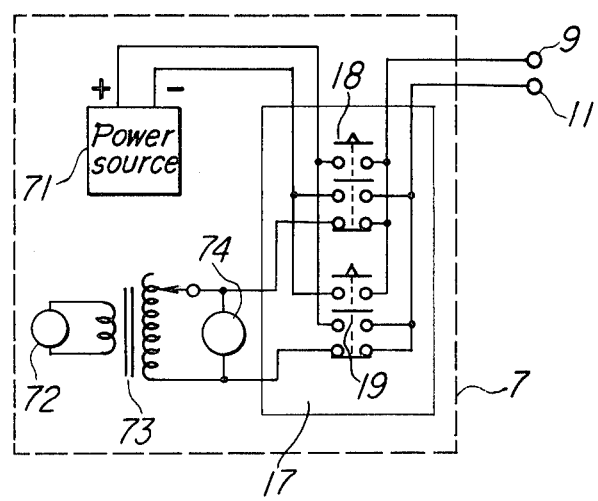
FIG. 4 is a circuit diagram for the power source system used in the apparatus shown in FIG. 1.

FIG. 4 shows an electrophoretic measuring apparatus using another embodiment of the power source system 7.

The power source system 7 shown in FIG. 4 comprises a constant current DC power source 71 rated at 10 mA for applying, to the sample, an electric field causing electrophoresis and a variable transformer 73 connected to an AC power source 72 of commercial frequency and having an AC volt meter 74 for the output measurement, which are connected to each other in parallel by way of an output switching or conversion circuit 17. The power from the power source system 7 is supplied by way of output terminals 9, 11 to the electrodes 30, 31. The output switching circuit 17 comprises a positive DC relay switch 18 that is connected to apply a positive DC voltage to the electrodes 30, 31 when closed and a negative DC relay switch 19 that is conncted to apply a negative DC voltage to the electrodes 30, 31 when closed. The output switching circuit 17 is constituted such that the electrodes 30, 31 are connected by way of the variable transformer 73 to the AC power source 72 when both of the relay switches 18, 19 are opened. In the apparatus shown by FIG. 1, the temperature in the temperature constant bath 1 is set to 20° C.±0.1° C. by a temperature control device or thermocontroller 4 and a heater 15.

Experimental measurement using the electrophoretic or thermocontroller measuring apparatus having the power source system shown in FIG. 4 is explained.

The U-shaped glass tube 2 filled with physiological saline water as a sample is placed in the temperature constant bath 1. Then, the AC power source 72 is put to ON and AC is supplied to the current supply electrodes 30, 31 for about 10 min. while regulating the output by the variable transformer 73 so that the volt meter 74 indicates 108 V. (Both of the positive DC relay switch 18 and the negative DC relay switch 19 are kept OFF).

After the values indicated on the temperature indicator 33 is settled to attain the stabilized state, the positive DC relay switch 18 is turned ON thereby switching the current supply from AC to DC.

As the result of this procedure we can keep the good condition shown in the following.

The temperature in the U-shaped glass tube 2 shown by the temperature indicator 33 changes only within a range of 0.1° C. upon switching from AC to DC and the temperature is also kept at a constant level after the switching.

Figure 5:
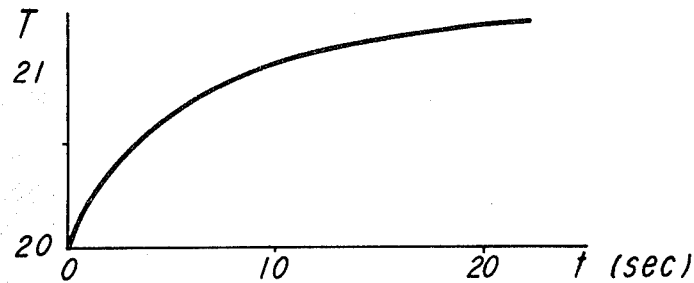
FIG. 5 is a chart showing temperature changes in a U-shaped glass tube in a conventional measuring apparatus.

For the reference, the temperature change with time in the U-shaped glass tube of a conventional apparatus where the DC is supplied to the electrodes only during measurement is shown in FIG. 5, in which ordinate indicates the temperature T(°C.) and abscissa indicates the time t (sec).

It is apparent also by reference to FIG. 5 that by the use of the apparatus and the method of this invention measurement can be performed under a constant temperature condition, whereby the measuring accuracy can significantly be improved.

In the actual measurement of the particle mobility, the following procedures are taken. A particle to be measured is determined during supply of the AC where the particles are in a stationary state and, when the temperature in the sample to be measured is well-stabilized, the positive DC relay switch 18 is put ON to measure the moving speed of the particle. Then, the negative DC relay switch 19 is put ON to measure the moving speed of the particle in the opposite direction. The mobility of one particle is determined as the average value for the moving speeds in the positive and the negative directions. Thereafter, other particles to be measured are selected and measurements are repeated again for several tens to several hundreds of particles both for the positive and the negative directions and the mobility is determined from the average value obtained therefrom.

Figure 6:
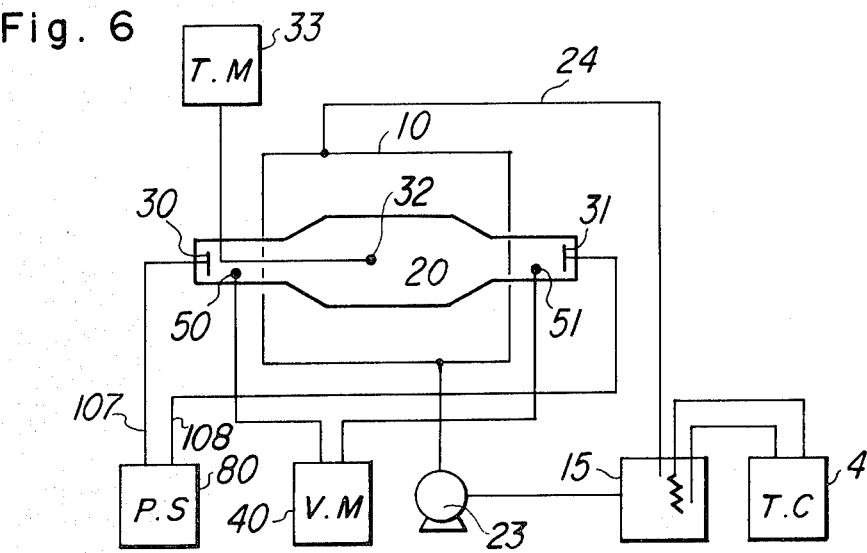
FIG. 6 is a schematic view of an electrophoretic measuring apparatus as a second embodiment according to this invention.
Figure 7:
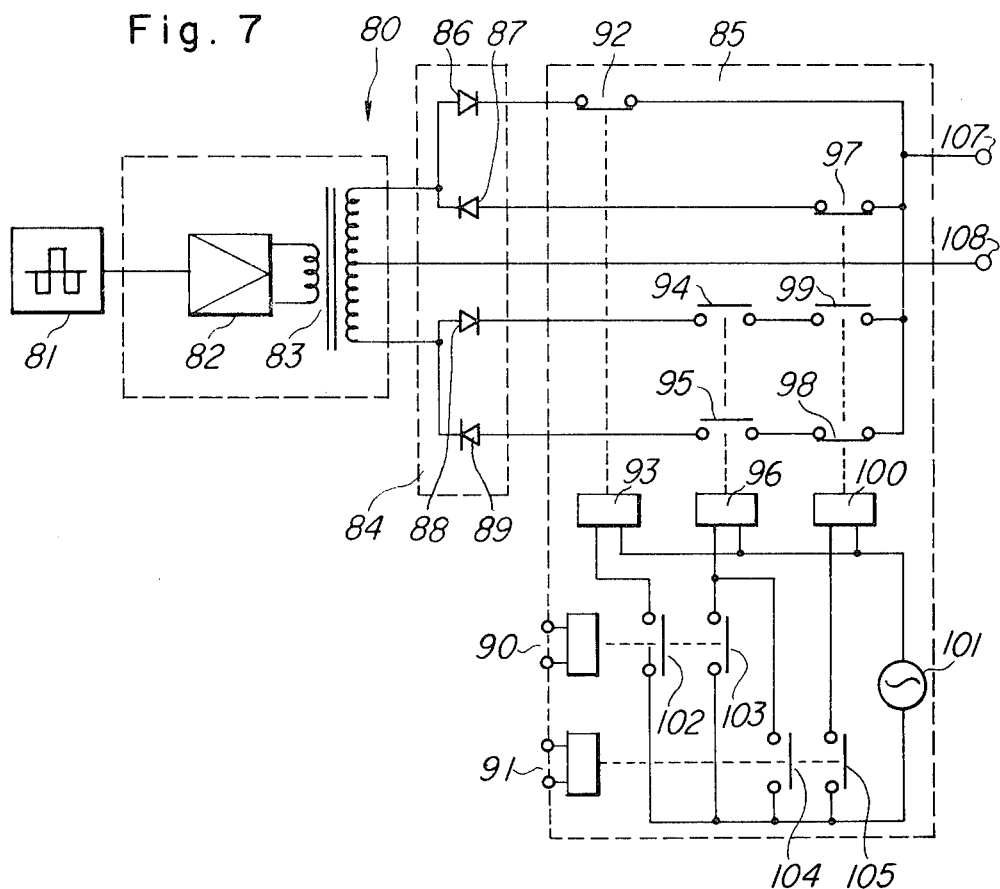
FIG. 7 is a circuit diagram for the power source system used in the apparatus shown in FIG. 6.

The apparatus and the method for measuring electrophoresis in the second embodiment of this invention is explained referring to FIG. 6 and FIG. 7.

The electrophoretic measuring apparatus comprises a square type measuring cell 20 of 0.7 mm depth and 7 mm height having at its outside a recycling bath 10 for cooling water, current supply electrodes 30, 31 disposed on respective ends and a power source system (P.S.) 80 for supplying power to them.

The recycling bath 10 is set to a temperature of 20° C. ±0.1° C. by water pipe 24 for recycling and motor 23, a temperature control device (T.C.) 4 and a heater 15.

The cell 20 is filled with culture solution "EAGLE" (registered trade mark) containing sheep red blood cells floating therein as the sample to be measured. Voltage detection electrodes (probes) 50, 51 are disposed in the inside of the current supply electrodes 30, 31 for the measurement of voltage by a DC volt meter (V.M.) 40 connected thereto. The power source system 80 comprises, as shown in FIG. 7, a rectangular waveform generator 81, an amplifier 82 for amplifying rectangular waveform signals from the generator 81, a pulse transformer 83 for stepping-up the rectangular voltage from the amplifier 82, a group of rectifiers 84 for rectifying the alternative rectangular power from the transformer 83 and a control circuit 85, the rectifier group 84 having diodes 86 to 89. The control circuit 85 comprises a relay switch 90 for positive DC indication, a relay switch 91 for negative DC indication, a relay 93 having a normally closed contact 92, a relay 96 having normally opened contacts 94, 95, and a relay 100 having normally closed contacts 97, 98 and normally opened contact 99, in which voltage from an AC power source 101 is applied to the relays 93, 96 and 100. The relay switches 90, 91 have normally opened contacts 102, 103, 104 and 105 respectively for controlling the current supplied from the AC power source 101 to the relays 93, 96, 100.

In the power source system 80, output terminals 107, 108 are connected to the current supply electrodes 30, 31 in which the output terminal 108 is directly led out from the center tap in the secondary windings of the transformer 83 and the output terminal 107 is connected to the output of the control circuit. The amplifier 82 is designed such that the amplifying factor can optionally be adjusted from the outside.

When none of the relay switches 90 and 91 is actuated, since none of the relays 93, 96, 100 is energized, current does not flow through the diodes 88, 89 but AC flows in the diodes 86, 87 alternately, whereby an AC voltage corresponding to the rectangular wave signals generated from the generator (oscillator) 81 is outputted to the output terminals 107, 108 and applied to the current supply electrodes 30, 31.

When the positive DC relay switch 90 is actuated by a sequence circuit (not shown), since the contacts 102, 103 are put ON to energize the relays 93, 96 which turns OFF the contact 92 and turns ON the contacts 94, 95, current of an identical polarity flows through the diodes 87, 89 alternately and a DC voltage is outputted to the output terminals 107, 108 and a positive DC voltage is applied to the current supply electrodes 30, 31.

In the opposite case where the negative DC relay switch 91 is actuated by the sequence circuit (not shown), since the contacts 104, 105 are turned ON to energize the relays 96, 100 which turns OFF the contacts 97, 98 and turns ON the contacts 94, 95, 99, current of an identical polarity flows through the diodes 86, 88 alternately in the direction opposite to the previous case. Thus a DC voltage is outputted to the output terminals 107, 108 and a negative DC voltage is applied to the current supply electrodes 30, 31.

The procedures for the electrophoretic measurement using said measuring apparatus are conducted in the same manner as previously explained for the first embodiment, in which the sequence circuit (not shown) supplies the operation voltage for the positive relay switch 90 and the negative relay switch 91 to proceed the supplying process for AC and DC (positive and negative polarities).

Figure 8:
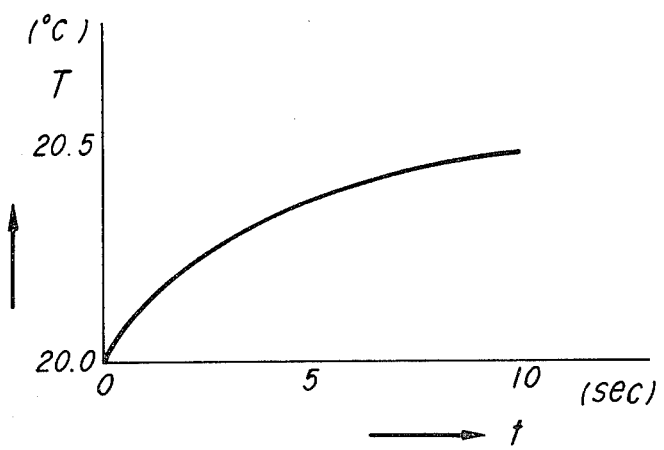
FIG. 8 is a chart showing temperature change in a measuring cell in a conventional measuring apparatus.

In the use of the above-mentioned power source system, the temperature change can be kept within the range of 0.1° C. and the voltage fluctuation can be kept less than 0.5 V upon AC and DC switching, and the temperature and the voltage are also kept constant with no changes thereafter. For the represence, in a case where 10 mA DC is supplied only during measurement in a conventional power source system, the voltage which was at 71.5 V at the start of the supply goes to 70 V and the temperature changes as shown in FIG. 8, in which the ordinate indicates the temperature T (°C) and abscissa indicates the time t (sec). As apparent from the result of the measurement, according to the measuring method of this invention using such an apparatus, measurement can be performed with excellently high accuracy in a short time under the stabilized temperature.

Figure 9:
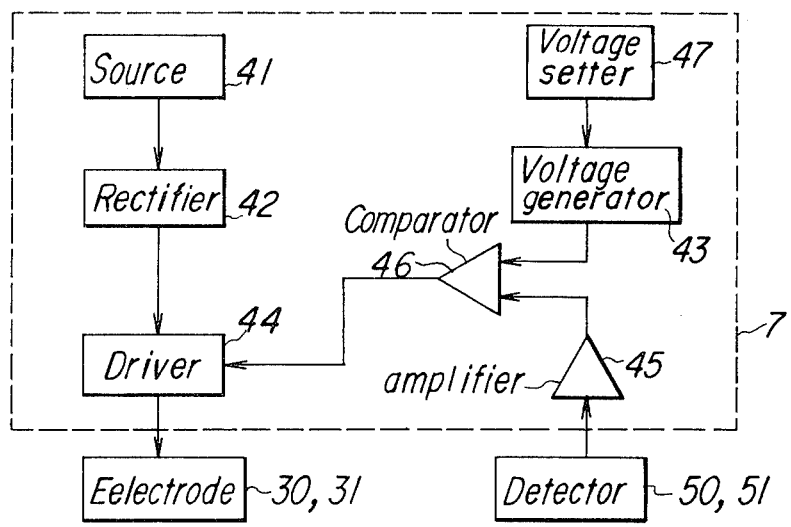
FIG. 9 is a block diagram showing another power source system for use with this invention.

Another embodiment of the power source system 7 for use with this invention is to be explained referring to FIG. 9, in which the system is adapted such that AC input (source) 41 is rectified through rectifier circuit 42 into a DC and outputted through a driver 44 as current output under the control of the information set to a voltage generator 43. The output is applied to the electrodes 30, 31 of the electrophoretic apparatus on the load. While on the other hand, the voltage between the voltage detection probes is fed back by way of terminals of the power source system connected to the voltage detection probes 50, 51 disposed in the migration chamber to the power source system. The feed back voltage is amplified in a high input impedance amplifier 45. The amplified voltage Va is compared in a comparison circuit (comparator) 46 with a voltage Vb set to a voltage generator 43 by an voltage setter 47 consisting, for example, of a potentiometer and the comparison result is outputted to the driver 44, so that the output current from the driver 44 is controlled in the direction of decreasing the current where Va is greater than Vb and in the direction of increasing the current where Va is smaller than Vb to thereby maintain the voltage constant between the voltage detection probes. The intensity of the electric field can thus be kept constant also following after the changes of the electrical resistance of the liquid. Further, direct control for the intensity of the electric field in the migration chamber is also possible to thereby improve the accuracy in the measurement of the electrophoretic mobility.

In addition, according to this invention, it is not always necessary to make the electrode surface area larger for the reduction in the impedance between the electrode and the liquid phase. This provides an advantage of increasing the degree of freedom in the structure of the electrophoretic apparatus, for example, partition means such as separation membranes can be provided between the migration chamber and the electrode so that the effect of the gases on the electrophoresis generated due to electrolysis at the electrodes can be eliminated.

Further, it is also possible in the apparatus of this invention to measure the sample irrespective of the impedance, if it is high, between the electrode and the sample or the sample of extremely high resistance, by using a small-sized voltage probes 50, 51 such as made of platinum in the migration chamber of the electrophoretic apparatus and setting the input impedance of the amplifier circuit connected to the voltage detection probes 50, 51 extremely high, for example, greater than $10^7 \Omega$.

Figure 10:
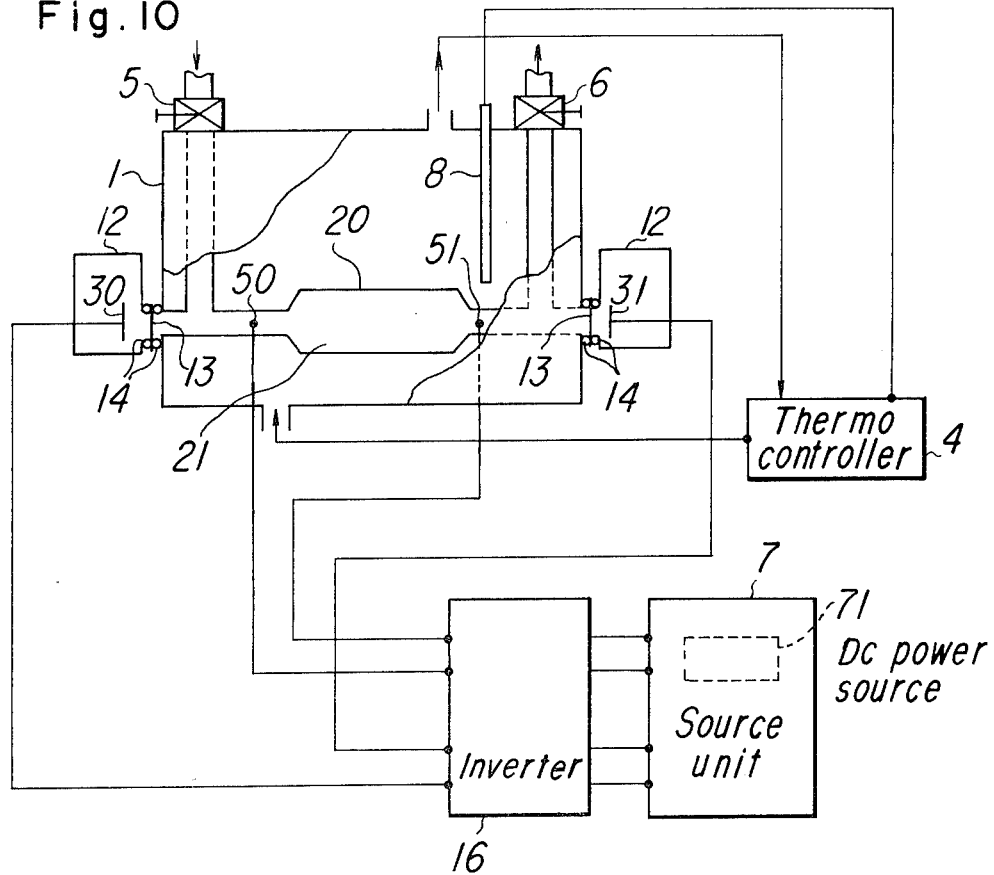
FIG. 10 is a schematic view of an electrophoretic measuring apparatus as a third embodiment using the power source shown in FIG. 9.

The third embodiment of the electrophoretic measuring apparatus using a microscope based on the embodiment shown in FIG. 9 is explained referring to FIG. 10.

The apparatus mainly comprises a migration chamber 20 disposed in a temperature constant bath 1 and electrodes 30, 31 connected on both ends of the migration chamber 20 for supplying current from the power source system 7 to the migration chamber 20.

The constant temperature bath 1 is equipped with a temperature control device 4 and adapted to keep the temperature constant in the migration chamber 20. The migration chamber 20 made of a cylindrical quartz of 7 mm×0.5 mm cross section and 80 mm length has at its both ends glass tubes each having a sample injection port 5 and a sample discharge port 6 respectively. Each of the opening ends of the glass tubes is connected by way of a gasket 14 and a partition membrane 13 to an electrolytic solution tank 12 containing phosphoric acid buffer solution and having electrodes 30, 31. The partition membrane 13 functions to prevent the effects of the gas on the electrophoresis generated upon electrolysis at the electrodes 30, 31. Further, the power source system 7 comprises a DC power source 71 designed to set a voltage Vb and a pair of platinum voltage detection probes 50, 51 disposed in the flow passage of the migration chamber 20. Thermometer 8 is disposed within the temperature bath 1. Power source system 7 further comprises a device for controlling the current supplied from the DC power source 71 to the electrodes 30, 31 so that decrease the current where Va is greater than Vb and increase the current where Va is smaller than Vb so that the voltage Va between the voltage detection probes is fed back to make the voltage constant and a polarity inverter (converter) 16 for carrying out the measurement of the electrophoresis both under the positive and the negative polarities.

Measuring procedures for the mobility using the electrophoretic measuring apparatus and the method are then explained.

The migration chamber 20 is placed in a constant temperature bath 1 having the temperature control device 4 and kept at a constant temperature. The sample is supplied to the migration chamber 20 by the opening and closure of the sample charge port 5 and the discharge port 6 that can automatically be opened and closed and, when the temperature of the sample is stabilized, a DC is supplied to the electrodes 30, 31 from the power source 7 so that the voltage between the voltage detection probes 50, 51 is constant. The DC power source 71 is constituted to be operated under the AC 100 V input and to output maximum 20 mA and 200 V.

Signals from the voltage detection probes 50, 51 are inputted into a polarity converter 16 so as to control its polarity and then put into the comparative controlling circuit (not shown) in power source unit 7. By means of said circuit, output from DC power source 71 is controlled, and then the output is applied into electrodes 30, 31 through the polarity converter.

The sample in the migration chamber 20 is moved by the electric field applied between the electrodes 30, 31 and the mobility based on the moving speed under the positive and negative electric fields is measured microscopically using an optical source. The microscope (not shown) is located at such a position that the movement of the particles in the migration chamber 20 can be observed.

Figure 11:
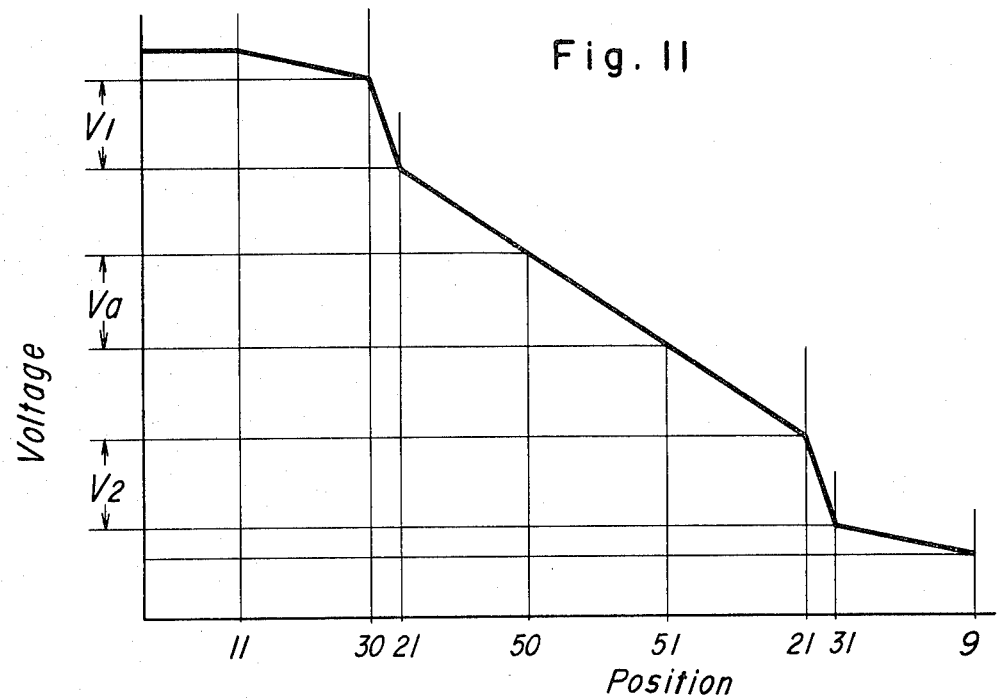
FIG. 11 is a characteristic graph showing the voltage distribution in each of the sections of the power source system for use with this invention.

Electrical gradient in the migration chamber is shown in FIG. 11. Since current is controlled depending on the voltage Va between the voltage detection probes in this apparatus, compensation is made for the voltage drop $V_1 + V_2$ between the electrodes 30, 31 and the sample to be measured. Mobility for each of the particles is determined by the average value for the mobility of each of the particles in the positive and negative electric fields.

The conditions for the electrophoretic experiment are as follows:
  Sample to be measured: red blood cell of sheep
  Floating liquid: phosphoric acid buffer solution $(15 \times 10^{-3} \text{ V/cm})$
  Migration temperature: 20° C.
  Voltage between voltage detection probes: 70 V
  Number of measured samples: 50
  Measuring time: 2 sec
  Mobility of 0.93 (micron/sec)/(V/cm)(average value for 50 samples) was obtained as the result of the electrophoretic measurement. The voltage Va between the voltage detection probes could be kept within 70 V±0.5 V and the error due to the voltage fluctuation could be restricted below ±0.7% during the above measurement. Since the voltage fluctuation was 67.5–70.0 V and the error was ±2% in the measurement using the electrophoretic apparatus of constant current system under the same conditions, the advantageous effects of this invention is apparent.

Figure 12:
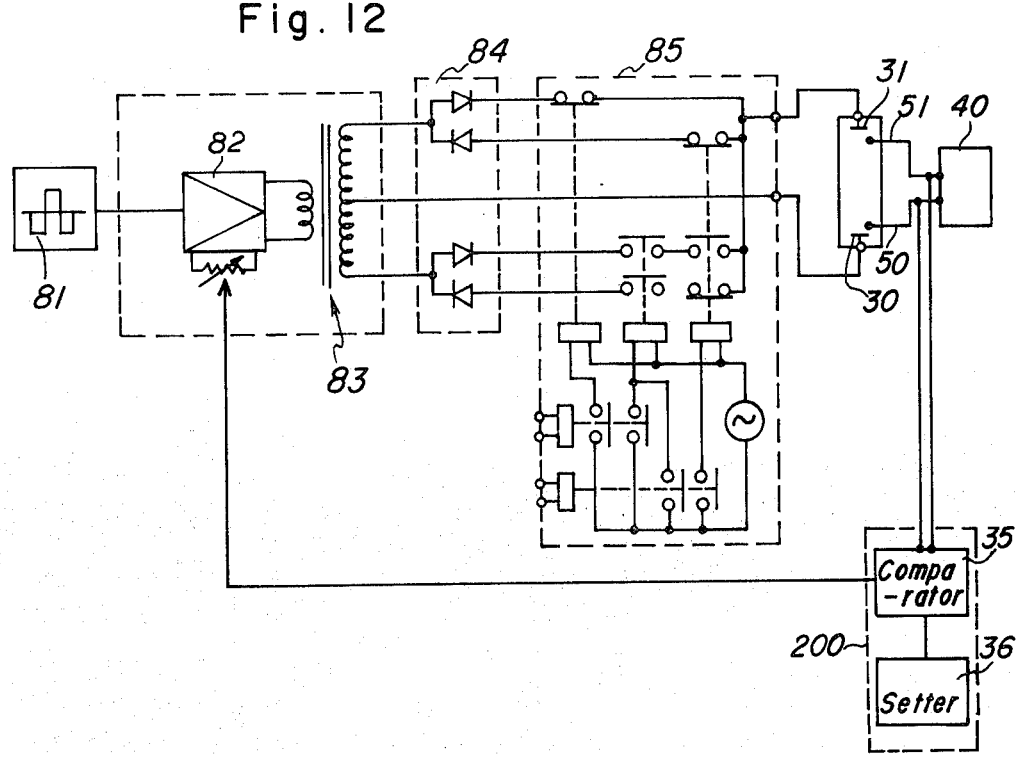
FIG. 12 is a schematic view of an electrophoretic measuring apparatus as a fourth embodiment according to this invention.

The fourth embodiment of this invention is explained referring to FIG. 12. The electrophoretic measuring apparatus additionally comprises a control circuit 200 that determines the amplifying factor of the amplifier 82 shown in the second embodiment by sensing the detection voltage between the voltage detection probes 50, 51 instead of controlling the amplifying factor externally. The control circuit 200 comprises a voltage setter 36 to which a reference voltage can be set externally, and a controller (comparator) 35 which compares the voltage set by the setter 36 with the detection voltage to control the gain of amplifier 82 so as to make the difference to zero. The same experiment as that with second embodiment was carried out using this apparatus. As the result, the voltage fluctuation could be kept within 0.3 V. This apparatus enables measurement at high accuracy under a constant temperature and an essentially constant electric field.

What is claimed is:
1. A method of observing electrophoretic phenomena of charged particles in a sample, comprising:
  a first step of preheating the sample by supplying an alternating current to the sample at a frequency high enough to keep the charged particles in the sample substantially stationary; and
  a second step of supplying a direct current to the sample thus preheated so as to observe the electrophoretic phenomena, and maintaining the electric power dissipation in the sample due to the direct current substantially equal to the electric power dissipation in the sample due to the alternating current.

2. The method according to claim 1, wherein the frequency of the alternating current is more than 10 Hz.

3. The method according to claim 2, wherein an electrophoretic mobility of the charged particles in the sample is microscopically observed in the second step.

4. The method according to claim 1, 2 or 3,
  wherein the sample is accommodated in a chamber having a first pair of electrodes; and
  wherein either alternating current or direct current is supplied to the sample through the first pair of electrodes in the first step or in the second step respectively.

5. The method according to claim 4, wherein the chamber has a second pair of electrodes at fixed locations thereof between the first pair of electrodes; and
  wherein the direct current supplied through the first pair of electrodes is controlled so that the voltage detected between the second pair of electrodes is kept constant in the second step.

6. An apparatus for observing electrophoretic phenomena of charged particles in a sample, comprising:
  a chamber for accommodating the sample, the chamber having a set of electrodes; and
  an electric power supply system for supplying either alternating or direct current to the sample through said set of electrodes, the electric power supply system having an alternating current power supply for delivering the alternating current so as to preheat the sample, a direct current power supply for delivering the direct current so as to observe the electrophoretic phenomena, and an output selection circuit for selectively supplying the alternating or direct current to the sample through said set of electrodes;

wherein the alternating current has a frequency high enough to keep the charged particles in the sample substantially stationary, and a magnitude such that the electric power dissipation in the sample due to the alternating current is substantially equal to the electric power dissipation in the sample due to the direct current.

7. The apparatus according to claim 6, wherein the frequency of the alternating current is more than 10 Hz.

8. The apparatus according to claim 7, wherein the apparatus is constituted so that an electrophoretic mobility of the charged particles in the sample is microscopically observable.

9. The apparatus according to claim 6, 7 or 8, wherein said set of electrodes comprises a first pair of electrodes through which either the alternating or direct current is supplied to the sample when either the alternating or direct current power supply is selected by the output selection circuit respectively, and a second pair of electrodes disposed at fixed locations of the chamber between the first pair of electrodes; and wherein the apparatus further comprises a control device for controlling the direct current supplied to the sample through the first pair of electrodes so that a direct voltage detected between the second pair of electrodes is kept constant.

* * * * *